United States Patent [19]

Nnadi et al.

[11] 4,049,565

[45] Sept. 20, 1977

[54] SUBSTITUTED MALEIMIDE LUBRICANT ADDITIVES AND LUBRICANT COMPOSITIONS MADE THEREWITH

[75] Inventors: John C. Nnadi, Lagos, Nigeria; Phillip S. Landis, Woodbury, N.J.

[73] Assignee: Mobil Oil Corporation, New York, N.Y.

[21] Appl. No.: 627,726

[22] Filed: Oct. 31, 1975

[51] Int. Cl.$^2$ .............................................. C10M 1/32
[52] U.S. Cl. ............................ 252/51.5 A; 252/33; 252/47.5; 260/326.5 R; 260/326.5 A; 260/326.5 SF; 260/326.5 FM; 260/326.5 M
[58] Field of Search ............... 252/33, 47.5, 51.5 A; 260/326.5 R, 326.5 A, 326.5 SF, 326.5 FM, 326.5 M

[56] References Cited

U.S. PATENT DOCUMENTS

| | | | |
|---|---|---|---|
| 2,412,557 | 12/1946 | Blair | 252/51.5 A |
| 2,412,708 | 12/1946 | Blair | 252/51.5 A |
| 2,526,517 | 10/1950 | Tawney | 260/326.5 FM X |
| 2,669,555 | 2/1954 | Giammaria | 252/51.5 A X |
| 2,676,179 | 4/1954 | Prill | 252/326.5 FM X |
| 2,727,862 | 12/1955 | Giammaria | 252/51.5 A |
| 2,958,672 | 11/1960 | Goldberg | 260/326.5 FM X |
| 3,135,765 | 6/1964 | Andress et al. | 252/51.5 A X |
| 3,367,864 | 2/1968 | Elliott et al. | 252/47.5 X |
| 3,397,210 | 8/1968 | Michalowicz | 260/326.5 FM |
| 3,401,117 | 9/1968 | Schiff | 252/33 |
| 3,431,204 | 3/1969 | Giammaria | 252/51.5 A X |
| 3,449,236 | 6/1969 | Engelhart | 252/51.5 A X |
| 3,714,045 | 1/1973 | Frangatos | 252/51.5 A |
| 3,725,434 | 4/1973 | Elliott et al. | 252/47.5 X |
| 3,810,913 | 5/1974 | Relles | 260/326.5 FM |
| 3,816,451 | 6/1974 | Crovetti et al. | 260/326.5 FM |
| 3,920,698 | 11/1975 | Haemmerle et al. | 260/326.5 A X |

FOREIGN PATENT DOCUMENTS

| | | | |
|---|---|---|---|
| 1,194,286 | 6/1970 | United Kingdom | 252/51.5 A |

*Primary Examiner*—Delbert E. Gantz
*Assistant Examiner*—Andrew H. Metz
*Attorney, Agent, or Firm*—C. A. Huggett; R. W. Barclay; C. E. Setliff

[57] ABSTRACT

Additives that are useful dispersants when placed in lubricants are prepared by (1) reacting an amine or a hydroxy amino compound, such as an amino alcohol, with a halomaleic anhydride and (2) reacting this product with an alkali or alkaline earth metal derivative of a substituted hydroxyaromatic compound.

18 Claims, No Drawings

SUBSTITUTED MALEIMIDE LUBRICANT ADDITIVES AND LUBRICANT COMPOSITIONS MADE THEREWITH

BACKGROUND OF THE INVENTION

1. Field of the Invention

The present invention is generally concerned with lubricant dispersants. More particularly, it is concerned with additives, and their use in lubricants as dispersants, of a product containing a hydroxyaromatic-substituted maleic anhydride moiety.

2. Discussion of the Prior Art

It is known that in the normal use of organic industrial fluids such as lubricating oils, transmission fluids, bearing lubricants, power transmitting fluids, and the like, the base medium is subjected to oxidizing conditions which can result in the formation of such things as sludge, lacquers and corrosive acids. These are undesirable at the least and can, under certain conditions, set up destructive forces not only toward the lubricant, but also toward the part being lubricated. That is to say, these oxidation residues or heavy contaminants may interfere with the normal operation of the fluid, increase its viscosity and even cause severe damage to the equipment itself.

In the lubrication of modern engines, it is particularly important that the oil composition be able to prevent acids, sludge and other solid contaminants from collecting at the point of contact of the moving parts. For example, poor piston travel and excessive engine bearing corrosion may result unless the oil can prevent oxidation products from depositing on the inner surfaces thereof.

One way of decreasing these difficulties is to add to the base organic fluid a detergent or dispersant additive that is capable of dispersing the solid particles to prevent them from interfering with the normal operation of any equipment being lubricated, leaving the lubricated surfaces relatively clean. The present invention is believed to solve the problem of dispersing solid contaminants with products that are not suggested by any prior art.

Metal-free nitrogen-containing dispersants are known in the art. For example, U.S. Pat. No. 3,445,386 discloses lubricant compositions containing polypropenyl-succinimide, -amides, -imidozolines and -imidozolidines, where the polypropenyl group is derived from polypropene having a number average molecular weight of from 500 - 3000. Exemplary of the compounds disclosed is:

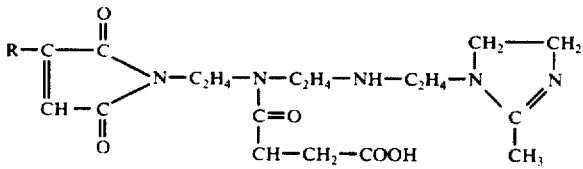

(1)

SUMMARY OF THE INVENTION

In accordance with this invention there is provided a compound of one of the formulas:

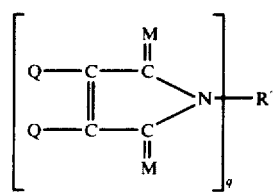

or

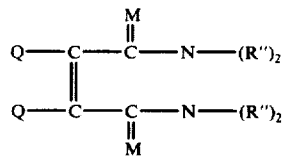

(2)

wherein Q is hydrogen or R-Ar-O- wherein Ar is an aromatic group, R is a polyalkylene group having a number average molecular weight of from about 500 to about 3000, only one Q being hydrogen, R' is hydrogen, alkyl, alkylene, aminoalkylene, hydroxyalkyl, hydroxyalkylene, aryl,

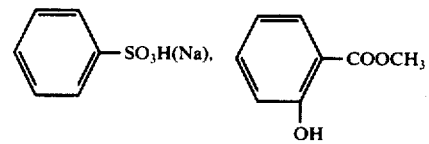

or alkyl-substituted aryl, R" may be the same or different and is hydrogen, alkyl, aminoalkyl, hydroxyalkyl, aryl or alkyl-substituted alkyl, $q$ is 1 or 2, and M is oxygen or two hydrogen atoms. The alkyl and alkylene portions may have from 1 to 30 carbon atoms. The aryl may have from 6 to 14 carbon atoms. The invention also provides lubricant compositions comprising said compounds.

DESCRIPTION OF SPECIFIC EMBODIMENTS

In general aspect, the compounds of the invention are made by first reacting a halomaleic anhydride with the appropriate reactant, e.g.

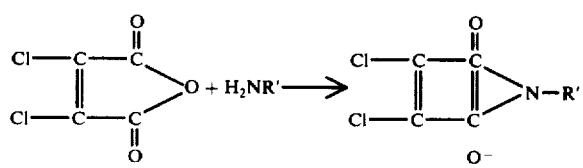

followed by reacting the final product with an alkali metal derivative of a substituted hydroxyaromatic compound, e.g.

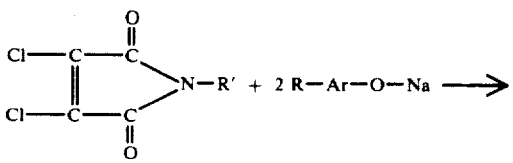

-continued

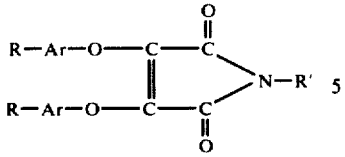

In formula (1) of the Summary, a compound in which q is 2 may be made by the following raction:

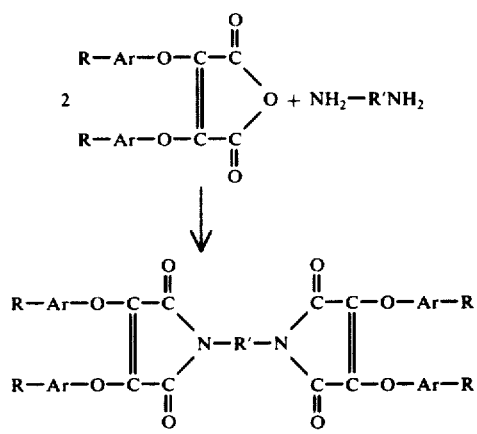

When carrying out the reaction between a halomaleic anhydride and amine or other appropriate compound in the first reaction, the halo portion of the anhydride may be any of the common halo groups, e.g. bromo, flouro or iodo and particularly chloro or bromo.

The amine reactant may be ammonia or a primary or a secondary amine having 1 to 250 carbon atoms. These can be made from halogenated polyolefins by reacting them with $NH_3$. As another class, polyalkylene polyamines may be used. The effective members include those of the formula:

$H_2N(RNH)_mH$ wherein R is a $C_2$–$C_5$ alkylene group and m is 1 to 10. Exemplary are ethylenediamine, diethylenetriamine, tetraethylenepentamine hexapropyleneheptamine, di(-methylethylene) triamine, and the like.

Amino-alchols may also be used. These include compounds of the formula:

$H_2NROH$ wherein R is a $C_1$–$C_5$ alkylene group. Examples of amino-alcohols are:
$NH_2(CH_2)_6OH$, $NH_2(CH_2)_2NH(CH_2)_2OH$,
$H_2NC_2H_4OH$, $NH(CH_2CH_2OH)_2$ and
$NH_2C(CH_2OH)_3$ In general aspect, the process for making the compounds will involve the following:

The halomaleic anhydride is first reacted with the amine and subsequently with the metal phenoxide. Typically, the halomaleic anhdride is reacted with the amine in a molar ratio of 1:2, 1:1 or 2:1 at temperatures of from about 0° C to about 200° C, preferably from about 20° C to about 150° C for about 1/2 hour to about 20 hours. Aromatic, polar or paraffinic solvents may be used and are desirable depending on the solubility properties of the imide or amide product. The reaction in cases of imide or di-amide formation leads to loss of water which is removed by distillation. It is believed that the above reaction of amine and halomaleic anhydride involves essentially an attack of the anhydride group by the amino group to yield the halomaleimides.

The reactant in the second step can be the alkali or alkaline earth metal derivative of a phenol, naphthol, resorcinol and anthrol substituted with a polyalkylene group. In addition to those listed, other substituted hydroxyaromatic compounds may be used.

The second step reaction is a simple nucleophilic displacement of halide by the phenoxide group. The phenoxide is added to the halomaleimide and the reaction mixture is stirred at from about 20° C to about 220° C, preferably from about 20° C to about 180° C, under a nitrogen atmosphere, for about 2 hours to about 48 hours. The reaction product is filtered, the filtrate washed and distilled to remove water using solvents used in the washing procedure. Washing may or may not be necessary to remove all traces of metal halide in the product. In most cases filtration alone is sufficient.

Products from the first step in all cases were shown to be authentic by elemental analysis for N and Cl and infrared spectra before being reacted with the preformed sodium phenoxides.

The additives of this invention can be used in a wide variety of lubricant media. Thus, they are effective agents for lubricating oils such as mineral oils, both naphthenic and paraffinic, including those containing substantial amounts of aromatic oils. They are also effective for synthetic oils, such as synthetic hydrocarbons, which are obtained by polymerizing olefins, synthetic esters and for polysiloxanes and the like. The term "lubricant" also includes greases made from any of the mentioned lubricating oils by adding a grease forming agent thereto. One particular ester oil of importance is one made by reacting an aliphatic monocarboxylic acid containing from 4 to 10 carbon atoms, preferably 5 to 9, with pentaerythritol. A widely used lubricating oil is made from monopentaerythritol and a mixed $C_5$ and $C_9$ acid.

Having described the invention in general terms, the following are offered as specific illustrations thereof. It will be strictly understood that the examples which follow are merely for illustration and are not be to construed in any way as limiting the invention. In the examples, "PB" is polybutneyl. Also, yields in the Examples include the weight of the process oil.

EXAMPLE 1

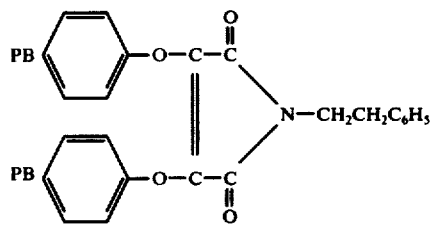

16.8 g of dichloromaleic anhydride was reacted with 12.1 g of phenethylamine in refluxing toluene. 1.6 ml of $H_2O$ was azeotroped off. To 13.5 g of the above maleimide product mixed with 100 g of diluent process oil at 50° C was added 420 g of sodium polybutenylphenoxide (50% active; number average molecular weight of active ingredient was 2100), and the reaction was heated at 120° C for 4 hours, then at 150–180° under $N_2$ atmosphere for another 4 hours. The reaction mixture was

EXAMPLE 2

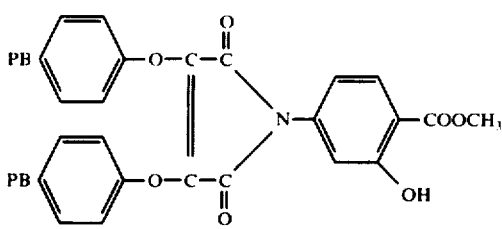

The maleimide was made in accordance with Example 1 using dichloromaleic anhydride and methyl-4-aminosilicilate. 16 g of this product was placed in 100 g of process oil and 420 g of the phenoxide of Example 1 was reacted as directed in that Example. The yield was 512 g.

EXAMPLE 3

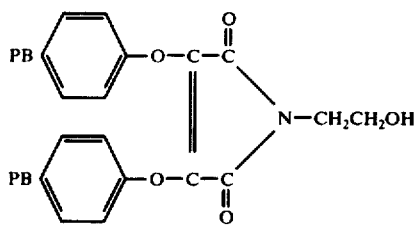

From 10 g of the maleimide of dichloromaleic anhydride and ethanol amine, 100 g of process oil and 420 g of the sodium phenoxide of Example 1, reacted as in that Example, 503 g of product was obtained.

EXAMPLE 4

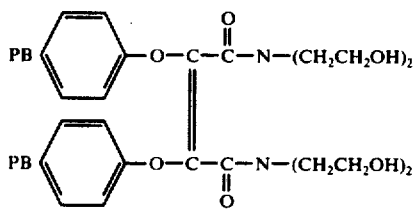

Using 18 g of the diamide made from two moles diethanolamine and one mole of dichloromaleic anhydride, 100 g of process oil and 420 g of the sodium phenoxide of Example 1, reacted as in that Example, 520 g product was obtained.

EXAMPLE 5

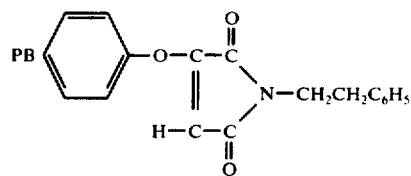

The procedure of Example 1 was followed except that the maleimide was made from monochloromaleic anhydride and phenethylamine and this was reacted with the sodium phenoxide in a 1:1 molar ratio.

EXAMPLE 6

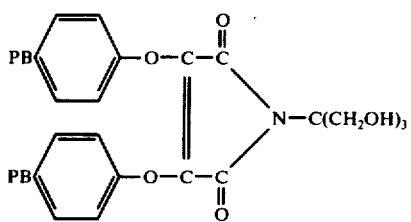

Made as shown in Example 1, except that trishydroxymethyl aminomethane was used in place of phenethylamine.

EXAMPLE 7

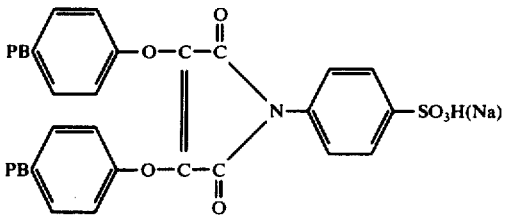

The procedure of Example 1 was followed except that the sodium salt of sulfanilic acid was used in place of phenethylamine.

EXAMPLE 8

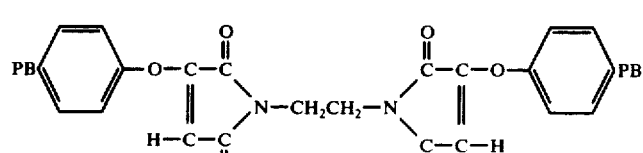

Made by the procedure of Example 1, except that the bis-imide of ethylenediamine and chloromaleic anhydride was used as the maleimide intermediate.

EXAMPLE 9

The procedure of Example 1 was followed, making a compound as depicted, except that the sodium phenoxide number average molecular weight was about 1000.

EXAMPLE 10

Same as Example 9 except that the number average molecular weight was about 600.

EVALUATION OF PRODUCTS

Diesel Oil Test

The additives were blended in oil and subjected to the diesel oil test. This test was developed to produce deposits from the oxidation of lubricating oil under conditions which closely approximate those found in the piston zone of a diesel engine. The test comprises an aluminum cylinder heated by radiant energy from an internal heater. The surface temperature of the cylinder is maintained at 575° F during the test period (140 minutes). The shaft turns slowly (2 RPM) and dips into an oil sump where it picks up a thin film of oil. This thin film is carried into the oxidation zone where heated gases (moist air at 350° F is typically employed, but nitrogen oxides, sulfur oxides and others can be used) form oxidation deposits. These deposits can be affected by the detergent as the test cylinder rotates into the sump. The efficiency of the detergent is rated by the color and intensity of the deposit on the shaft at the end of the test. The results obtained are shown in the table below.

Carbon Removal Test

Broadly, the test involves making a carbon blackmineral oil dispersion using an ultrasonic device, depositing this dispersion on a bed of carefully screened metal powder (we used nickel), and running test oil through this powder to determine amount of carbon removed.

More specifically, a precisely measured quantity of solvent oil (oil with no additive and no carbon black) is worked through the metal bed and allowed to equilibrate at a temperature of about 210° F. Then a precisely measured amount of the carbon black-base oil dispersion is allowed to flow through the bed at a precisely controlled rate. The carbon black-mineral oil dispersion that has flowed through the bed is collected. Next, the test oil containing the additive is run through the now carbon-coated bed at a precise rate and the fluid is collected after it has gone through the bed. The optical density of the carbon-based oil is taken at 540 m$\mu$ before and after being put through the bed. The difference in optical densities gives a measure of the carbon removed.

Results using this test are shown in the table below.

|  | Diesel Oil Test Results (140 mins.) 100=clean; 50=heavy lacquer | Carbon Removal Test R100% Carbon Removal |
| --- | --- | --- |
| Oil[1][2] | 60 | 1 |
| Oil + 4% by weight of Ex. 1 | 79 | — |
| Oil + 4% by weight of Ex. 2 | 70 | — |
| Oil + 4% by weight of Ex. 3 | — | 37 |
| Oil + 4% by weight of Ex. 4 | — | 40 |

[1]55% by weight of a 200 second solvent paraffinic neutral mineral oil and 37% by weight of a 125 second solvent paraffinic bright mineral oil.
[2]Contains an additive package comprising an antioxidant and an extreme pressure agent.

We claim:

1. A compound of the formula:

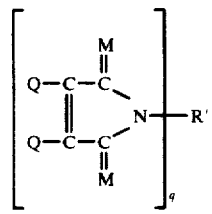

wherein Q is hydrogen or R-AR-O wherein Ar is selected from the group consisting of phenyl, naphthyl, resorcinyl and anthryl, R is a polyalkylene group having a number average molecular weight of from 500 to 3000, only one Q being hydrogen, R' is hydrogen, alkyl, alkylene, aminoalkylene hydroxyalkyl, hydroxyalkylene, aryl,

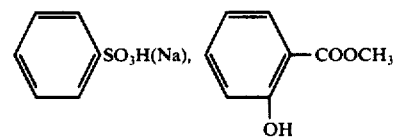

or alkyl-substituted aryl, q is 1 or 2 and M is oxygen.

2. The compound of claim 1, wherein R is polybutenyl having a number average molecular weight of about 2000 and Ar is phenyl.

3. The compound of claim 2 wherein q is 1, M is oxygen, both of Q are R-Ar-O- and R' is —CH$_2$CH$_2$C$_6$H$_5$.

4. The compound of claim 2 wherein q is 1, M is oxygen, both of Q are R-Ar-O- and R' is

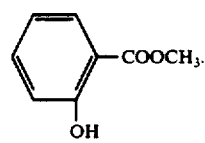

5. The compound of claim 2 wherein q is 1, M is oxygen, both of Q are R-Ar-O- and R' is —CH$_2$CH$_2$OH.

6. The compound of claim 2 wherein q is 1, M is oxygen, one of Q is R-Ar-O- and R' is —CH$_2$CH$_2$C$_6$H$_5$.

7. The compound of claim 2 wherein q is 1, M is oxygen, both of Q are R-Ar-O- and R' is —C(CH$_2$OH)$_3$.

8. The compound of claim 2 wherein q is 1, M is oxygen, both of Q are R-Ar-O- and R' is

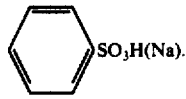

9. The compound of claim 2 wherein q is 2, M is oxygen, one Q is R-Ar-O- and R' is —CH$_2$CH$_2$—.

10. A lubricant composition comprising a major proportion of an oil of lubricating viscosity or a grease thereof and a detergency amount of a compound of the formula:

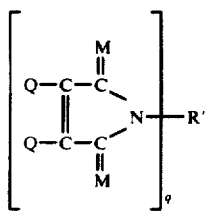

wherein Q is hydrogen or R-Ar-O wherein Ar is selected from the group consisting of phenyl, naphthyl, resorcinyl and anthryl, R is a polyalkylene group having a number average molecular weight of from 500 to 3000, only one Q being hydrogen, R' is hydrogen, alkyl, alkylene, aminoalkylene hydroxyalkyl, hydroxyalkylene, aryl,

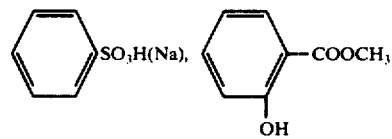

or alkyl-substituted aryl, $q$ is 1 or 2 and M is oxygen.

11. The composition of claim 10 wherein R has a number average molecular weight of about 2000 and Ar is phenyl.

12. The composition of claim 11 wherein $q$ is 1, M is oxygen, both of Q are R-Ar-O- and R' is —CH$_2$CH$_2$C$_6$H$_5$.

13. The composition of claim 11 wherein q is 1, M is oxygen, both of Q are R-Ar-O- and R' is

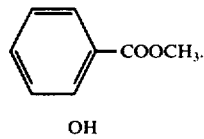

14. The composition of claim 11 wherein q is 1, M is oxygen, both of Q are R-Ar-O- and R' is —CH$_2$CH$_2$OH.

15. The composition of claim 11 wherein q is 1, M is oxygen, one Q is R-Ar-O- and R' is —CH$_2$CH$_2$C$_6$H$_5$.

16. The composition of claim 11 wherein q is 1, M is oxygen, both of Q are R-Ar-O- and R' is —C(CH$_2$OH)$_3$.

17. The composition of claim 11 wherein q is 1, M is oxygen, both of Q are R-Ar-O- and R is

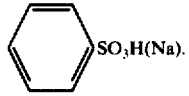

18. The composition of claim 11 wherein q is 2, M is oxygen, one Q is R-Ar-O- and R' is —CH$_2$CH$_2$—.

* * * * *